United States Patent
Cromer et al.

(10) Patent No.: US 7,600,054 B2
(45) Date of Patent: Oct. 6, 2009

(54) APPARATUS, SYSTEM, AND METHOD FOR PROTECTING A MOTION-SENSITIVE DEVICE

(75) Inventors: Daryl Carvis Cromer, Apex, NC (US); Howard Jeffrey Locker, Cary, NC (US); Tin-Lup Wong, Chapel Hill, NC (US)

(73) Assignee: Lenovo Singapore Pte Ltd, Singapore (SG)

( * ) Notice: Subject to any disclaimer, the term of this patent is extended or adjusted under 35 U.S.C. 154(b) by 419 days.

(21) Appl. No.: 11/273,240

(22) Filed: Nov. 14, 2005

(65) Prior Publication Data
US 2007/0107518 A1    May 17, 2007

(51) Int. Cl.
G06F 3/00 (2006.01)
G11B 15/04 (2006.01)
G11B 19/04 (2006.01)

(52) U.S. Cl. .................. 710/18; 710/6; 360/60

(58) Field of Classification Search ......... 710/18
See application file for complete search history.

(56) References Cited

U.S. PATENT DOCUMENTS

| | | | |
|---|---|---|---|
| 5,481,733 A | 1/1996 | Douglis et al. | 395/750 |
| 5,774,292 A | 6/1998 | Georgiou et al. | 360/73.03 |
| 5,954,820 A | 9/1999 | Hetzler | 713/323 |
| 6,603,620 B1 * | 8/2003 | Berding | 360/60 |
| 6,791,799 B2 | 9/2004 | Fletcher | 360/255 |
| 2006/0044668 A1 * | 3/2006 | Cho | 360/75 |

* cited by examiner

*Primary Examiner*—Alford W Kindred
*Assistant Examiner*—Zachary K Huson
(74) *Attorney, Agent, or Firm*—Kunzler & McKenzie; Carlos Muniz-Bustamante

(57) ABSTRACT

An apparatus, system, and method are disclosed for protecting a motion-sensitive device. The apparatus includes an identification module, a determination module, and a scheduler. The identification module identifies a use-intensive task involving the motion-sensitive device. The determination module determines a motion forecast that predicts a substantially motionless time interval. The scheduler schedules the use-intensive task such that the use-intensive task executes within the substantially motionless time interval. In this manner, a historical movement pattern is used to schedule future tasks such that the coincidence of task use of the motion-sensitive device and movement of the motion-sensitive device is minimized.

22 Claims, 6 Drawing Sheets

APPARATUS, SYSTEM, AND METHOD FOR PROTECTING A MOTION-SENSITIVE DEVICE

BACKGROUND OF THE INVENTION

1. Field of the Invention

This invention relates to portable computing devices and more particularly relates to protecting motion-sensitive devices within the portable computing devices.

2. Description of the Related Art

The capabilities and complexity of portable computing devices continues to increase. More and more computing functionality is performed using portable computing devices such as laptops, Personal Digital Assistants (PDAs), portable music players, cell phones, tablet PCs, and the like. Other computing systems are used in contexts where motion of the computing system is inherent. For example, vehicle mounted or installed computer systems and robots may include standard or compact computing devices installed.

Typically, these computing devices include one or more internal devices having mechanically moving parts. Even devices, such as a PDA, that ordinarily include internal devices with non-moving parts may temporarily include a storage device such as a microdrive, that includes mechanically moving parts. The devices having mechanically moving parts that are internal to, or operate in conjunction with, the computing devices are referred to herein as "motion-sensitive devices."

Unfortunately, motion-sensitive devices remain highly susceptible to serious damage when operation of the motion-sensitive device is combined with movement of the motion-sensitive device itself. Typically, movement of the computing device also moves the motion-sensitive device. These movements may include careful calculated movements, bumping, jarring, drops, movement of the base on which the computing device rests, and the like. Often, these movements adversely affect the movement of the internal parts of the motion-sensitive device. The interference caused by movement of the computing device can cause serious damage to the internal moving parts as well as to other parts in the motion-sensitive device.

The actual damage caused as well as the probability for damage due to movement of the motion-sensitive device is typically greatest during periods of time when the motion-sensitive device is most active and the motion-sensitive device is simultaneously in motion. Placing the motion-sensitive device in motion increases the likelihood of a damaging movement. Operating the motion-sensitive device during the movement enhances the risk that damage will result from movement of the motion-sensitive device. Limiting the movement of the motion-sensitive device during periods of high use of the motion-sensitive device is inconvenient and often impractical because users place such a high value on portability of the computing device.

From the foregoing discussion, it should be apparent that a need exists for an apparatus, system, and method for protecting a motion-sensitive device. Beneficially, such an apparatus, system, and method would minimize operation of the motion-sensitive device during time periods when the computing device is likely to be in motion. The apparatus, system, and method would schedule and/or advise use-intensive tasks involving the motion-sensitive device during substantially motionless time intervals for the computing device.

SUMMARY OF THE INVENTION

The present invention has been developed in response to the present state of the art, and in particular, in response to the problems and needs in the art that have not yet been fully solved by currently available portable computing devices. Accordingly, the present invention has been developed to provide an apparatus, system, and method for protecting a motion-sensitive device that overcome many or all of the above-discussed shortcomings in the art.

The apparatus is provided with a logic unit containing a plurality of components configured to functionally execute the necessary steps. These components in the described embodiments include an identification module, a determination module, and a scheduler.

The identification module identifies a use-intensive task involving the motion-sensitive device. A monitor may monitor use of the motion-sensitive device by at least one operating task. The monitor may measure based on a variety of measures such as number of accesses per unit of time. A task manager may record use data representative of use of the motion-sensitive device by the at least one operating task. The task manager may also classify the one or more operating tasks as use-intensive tasks according to a use threshold.

The determination module determines a motion forecast that predicts a substantially motionless time interval. The scheduler schedules the use-intensive task such that the use-intensive task executes within the substantially motionless time interval.

The determination module may include a tracking module configured to track movements of the motion-sensitive device in relation to at least one reference time interval. A classification module of the determination module may classify the movements based on a severity threshold. A pattern generator may generate a movement pattern representative of movement of the motion-sensitive device during a predefined time period. A forecaster of the determination module may cooperate with the pattern generator to define a motion forecast having at least one substantially motionless time interval. The motion forecast is based at least in part on the movement pattern.

A system is also presented for protecting a motion-sensitive device. The system includes components substantially similar to those described above in relation to different embodiments of the apparatus. In addition, the system may include a hard disk drive, a processor, and an accelerometer. The accelerometer provides movement information to a pattern generator which generates a movement pattern. The forecaster may use the movement pattern to define a motion forecast. The schedule schedules a task that uses the hard disk drive during a substantially motionless time interval as indicated by the motion forecast.

A method is also presented for protecting a motion-sensitive device. The method in the disclosed embodiments substantially includes the steps necessary to carry out the functions presented above with respect to the operation of the described apparatus and system.

As used herein, the term "motion-sensitive device" refers to any device having mechanical, moving parts such that movement of the motion-sensitive device increases the risk of damage to the mechanical moving parts and/or other parts of the motion-sensitive device. Examples of motion-sensitive devices include Hard Disk Drives (HDD), microdrives, CD-ROMS and DVD-ROMS, including read/write versions, and the like. Those of skill in the art will recognize the variety of conventional and future technologies which may serve as a motion-sensitive device. As used herein, the term "use-intensive task" refers to any computing operation that uses, operates, interacts with, references, or causes operation of a computing device with a frequency above a predefined threshold.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced with fewer or more of the specific features or advantages of a particular embodiment. These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE INVENTION

Figure 1:
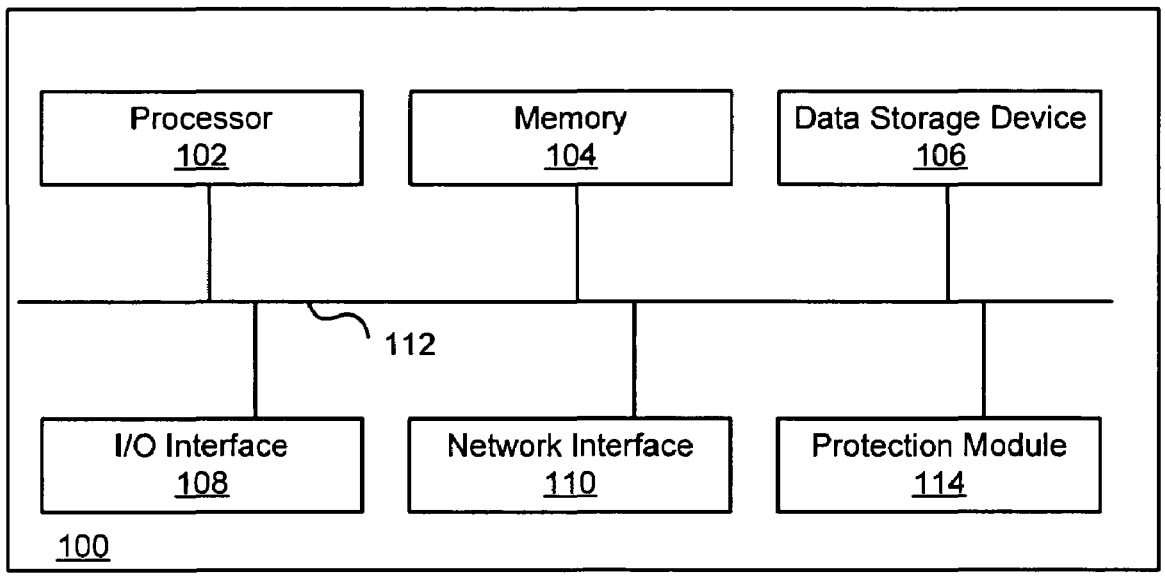
FIG. 1 is a schematic block diagram illustrating one embodiment of a computing system comprising one embodiment of the present invention.

FIG. 1 illustrates a system 100 suitable for use with the present invention. The system 100 comprises a computing device having main components of a computer system including a processor 102, memory 104, one or more data storage devices 106, an Input/Output (I/O) interface 108, and one or more network interfaces 110. The main components may communicate over a communication bus 112. Those of skill in the art are well familiar with examples and versions of the main components 102, 104, 106, 108, 110 and the communication bus 112. These components will not be described in further detail, except to note that, the components maybe of various sizes including standard and miniature sizes and that the components may be permanently connected or removably connected to the system 100.

The I/O interface 108 may be connected to a display device and/or a user input device such as a keyboard, a mouse, speakers, a microphone, and the like. Similarly, the network interface 110 may connect to a wireless network such as a cellular network or computer network. Optionally, the network interface 110 may connect to a wired network as such a network is available. Preferably, the I/O interface 108 and network interface 110 facilitate the portability of the system 100.

The system 100 may also include a protection module 114 configured to monitor use and motion of motion-sensitive devices within the system 100. Based on the use and motion information for a motion-sensitive device, the protection module 114 controls use of the motion-sensitive devices by other components in the system 100. In the embodiment of FIG. 1, the protection module 114 may be configured to control use of one or more data storage devices 106. Examples of data storage devices 106 include CDROM drives, DVD drives, CDRW drives, DVDRW drives, Hard Disk Drives (HDD), and the like.

In systems 100 that are portable, operation of motion-sensitive devices 106 while these devices 106 are in physical motion increases the likelihood of damage due to bumping, jarring, and possibly dropping of the system 100. Other devices such as the processor 102, memory 104, I/O interface 108, and network interface 110 have few, if any, moving parts and are therefore not as susceptible to damage.

Advantageously, the protection module 114 is configured to protect the motion-sensitive devices 106 by limiting use of the motion-sensitive devices 106 to time periods when motion of the system 100 or devices 106 is less likely. Avoiding concurrent use and motion of the motion-sensitive devices 106 minimizes potential for damage to the motion-sensitive device 106. Where use of the motion-sensitive device 106 can not be limited without affecting user satisfaction, the protection module 114 may minimize use during movement by scheduling certain use-intensive tasks involving the motion-sensitive device 106 such that these tasks begin and complete during a forecaster period of non-motion of the motion-sensitive device 106.

Figure 2:
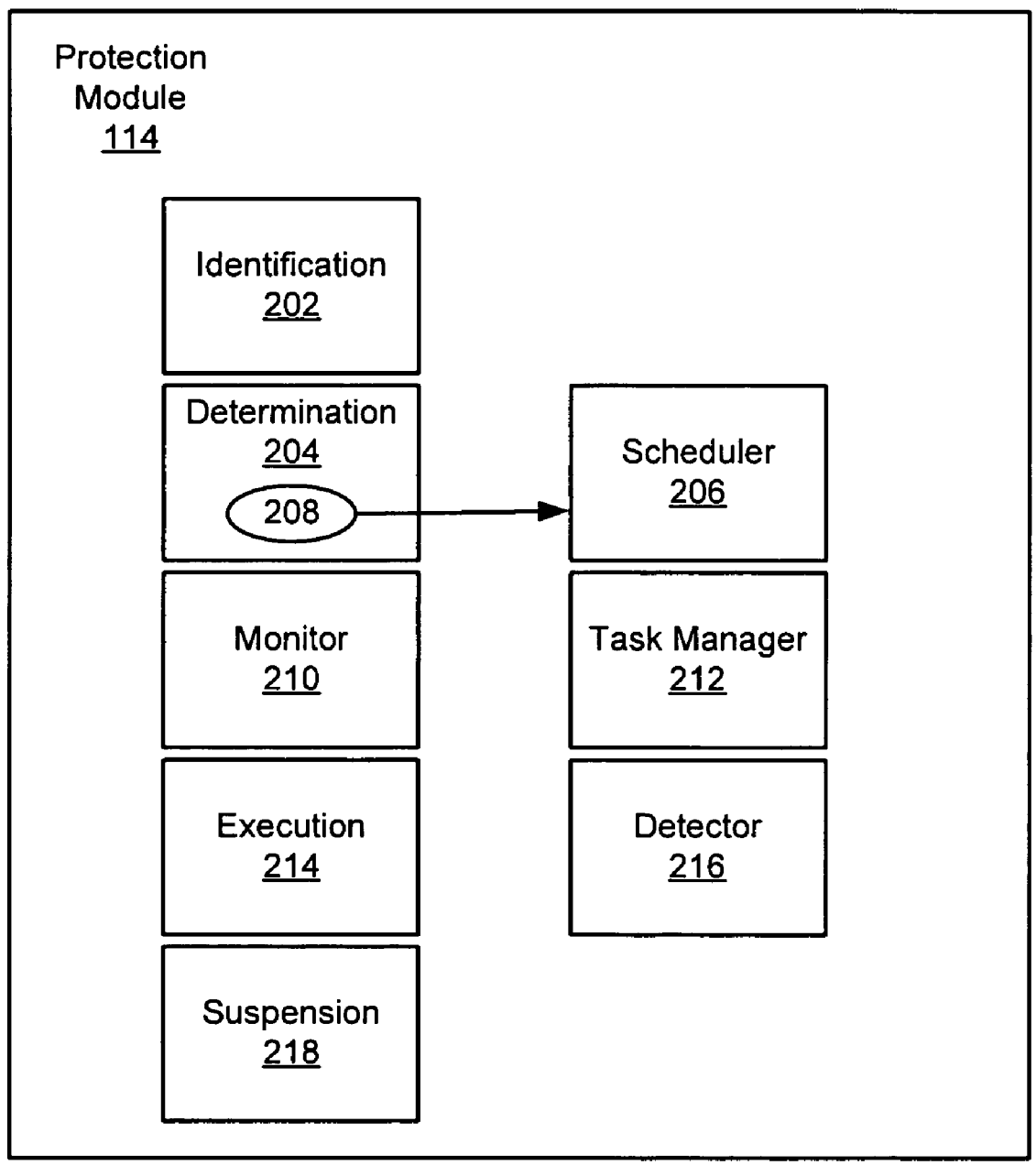
FIG. 2 is a schematic block diagram illustrating one embodiment of an apparatus for protecting a motion-sensitive device.

FIG. 2 illustrates one embodiment of a protection module 114. The protection module 114 may include an identification module 202, a determination module 204, and a scheduler 206. The identification module 202 identifies one or more use-intensive tasks involving the motion-sensitive device 106. The identification module 202 may identify use-intensive tasks automatically or through user input. If user input is used, the identification module 202 may also include a user interface. Alternatively, the identification module 202 interacts with an existing user interface to identify use-intensive tasks.

In one embodiment, use-intensive tasks are predefined and stored in a data structure accessible to the identification module 202. Examples of tasks that may be considered use-intensive tasks may include Hard Disk Drive (HDD) backup operations, HDD defragmentation operations, HDD virus and/or spyware scanning operations, HDD data migration operations, and the like. Those of skill in the art will recognize that the type of task considered use-intensive may change depending on the type of motion-sensitive device 106.

The determination module 204 determines a motion forecast 208 that predicts a substantially motionless time interval in the future for the motion-sensitive device 106. Preferably, the motion forecast 208 for the motion-sensitive device 106 correlates to the motion forecast 208 for the system 100. Alternatively, the motion-sensitive device 106 may be moveable independent of the system 100 and therefore have different motion forecast 208.

The determination module 204 may use a variety of techniques, described in more detail below, to determine a motion forecast 208. In one embodiment, the determination module 204 references a set of movement patterns recorded for a particular period of time. Typically, the movement patterns are historical information about the movement of the motion-sensitive device 106. A forecasting algorithm may use the movement patterns to predict the likelihood that the motion-sensitive device 106 will experience substantially no movement within a future time period.

The determination module 204 provides the motion forecast 208 to the scheduler 206. The scheduler 206 schedules use-intensive tasks such that the use-intensive task executes within the substantially motionless time interval predicted in the motion forecast 208. The scheduler 206 may automatically schedule the use-intensive tasks based on the motion forecast 208. Alternatively, the scheduler 206 cooperates with the user to schedule the use-intensive tasks.

Together the identification module 202, determination module 204 and scheduler 206 cooperate to ensure that use-intensive tasks are executed during periods of substantially no motion of the motion-sensitive device 106. Consequently, damage to the motion-sensitive device 106 and, in particular, to the moving parts within the motion-sensitive device 106 is minimized. The effectiveness of the protection module 114 depends at least in part on the accuracy of the motion forecast 208.

Certain embodiments of the protection module 114 may include additional optional modules such as a monitor 210, a task manager 212, an execution module 214, a detector 216, and a suspension module 218. Those of skill in the art recognize that these optional modules may be integrated with, or separate from, the protection module 114. Furthermore, functionality provided by these optional modules may alternatively, be provided by other modules in a system 100.

The monitor 210 and task manager 212 may cooperate to facilitate identifying use-intensive tasks. Preferably, the monitor 210 tracks, or monitors, use of the use-intensive device 106 by one or more operating tasks. The monitor 210 may comprise a software module monitoring Input/Output (I/O) traffic, such as reads and writes to and from a HDD 106, for example. Preferably, I/O traffic is monitored in relation to a period of time such as a second, a minute, an hour, or the like. The monitor 210 may communicate use data for a particular task to the task manager 212. The task manager 212 may record the use data. In addition, the task manager 212 may classify one or more of the operating tasks by comparing the use data with a use threshold.

Typically, a use-intensive task is a computing task that involves a use frequency above the use threshold. The use frequency may comprise the number of operations involving the motion-sensitive device 106 within a particular time period. The use threshold may be predefined and user configurable.

For example, where the motion-sensitive device 106 is a HDD 106, the use threshold may comprise about one-hundred reads and/or writes per minute. The monitor 210 may detect use of a HDD 106 above this threshold, for example two-hundred reads and/or writes per minute. The task manager 212 records the use data. Because the use threshold is exceeded, the task manager 212 classifies the task using the HDD 106 as a use-intensive task. In certain embodiments, the task manager 212 may include a plurality of classifications including high-use, low-use, average-use, and the like. Each classification may include an associated use threshold.

In certain embodiments, a user may adjust the values for the use thresholds. Alternatively, the user may adjust which classifications of tasks result in the scheduler 206 scheduling those tasks to operate during substantially motionless time intervals. In this manner, the user may control the level of risk the motion-sensitive device 106 is exposed to during movement of the system 100.

The execution module 214, detector 216, and suspension module 218 cooperate to further minimize damage risk for the motion-sensitive device 106. The execution module 214 executes the use-intensive task during one of the substantially motionless time intervals indicated by the motion forecast 208. Preferably, the motionless time interval is a specific time period within a particular twenty-four hour period. The motion forecast 208 may also indicate a particular time period within a particular day of the week. The execution module 214 may comprise a utility within an operating system such as a service or background process manager.

The detector 216 monitors motion of the motion-sensitive device 106 while the execution module 214 executes the use-intensive task within the motionless time interval. If the detector 216 detects motion of the motion-sensitive device 106 or motion above a suspension threshold, the detector 216 communicates with suspension module 218. The suspension threshold may be user configurable. In response to this communication, the suspension module 218 suspends operation of the use-intensive task. In one embodiment, the suspension module 218 sends an interrupt to the processor 102. In response to the interrupt, the processor 102 may interrupt operation of the task and place the task into a hibernation or suspended state.

The processor 102 may suspend the task for a specific period of time. Alternatively, the detector 216 and suspension module 218 may continue to communicate and monitor motion of the motion-sensitive device 106. If the motion-sensitive device 106 experiences a motionless period of predefined length, the suspension module 218 may signal the task to resume operation. Preferably, when the task suspends operation, the state of the task is preserved such that the task can be readily resumed.

Figure 3:
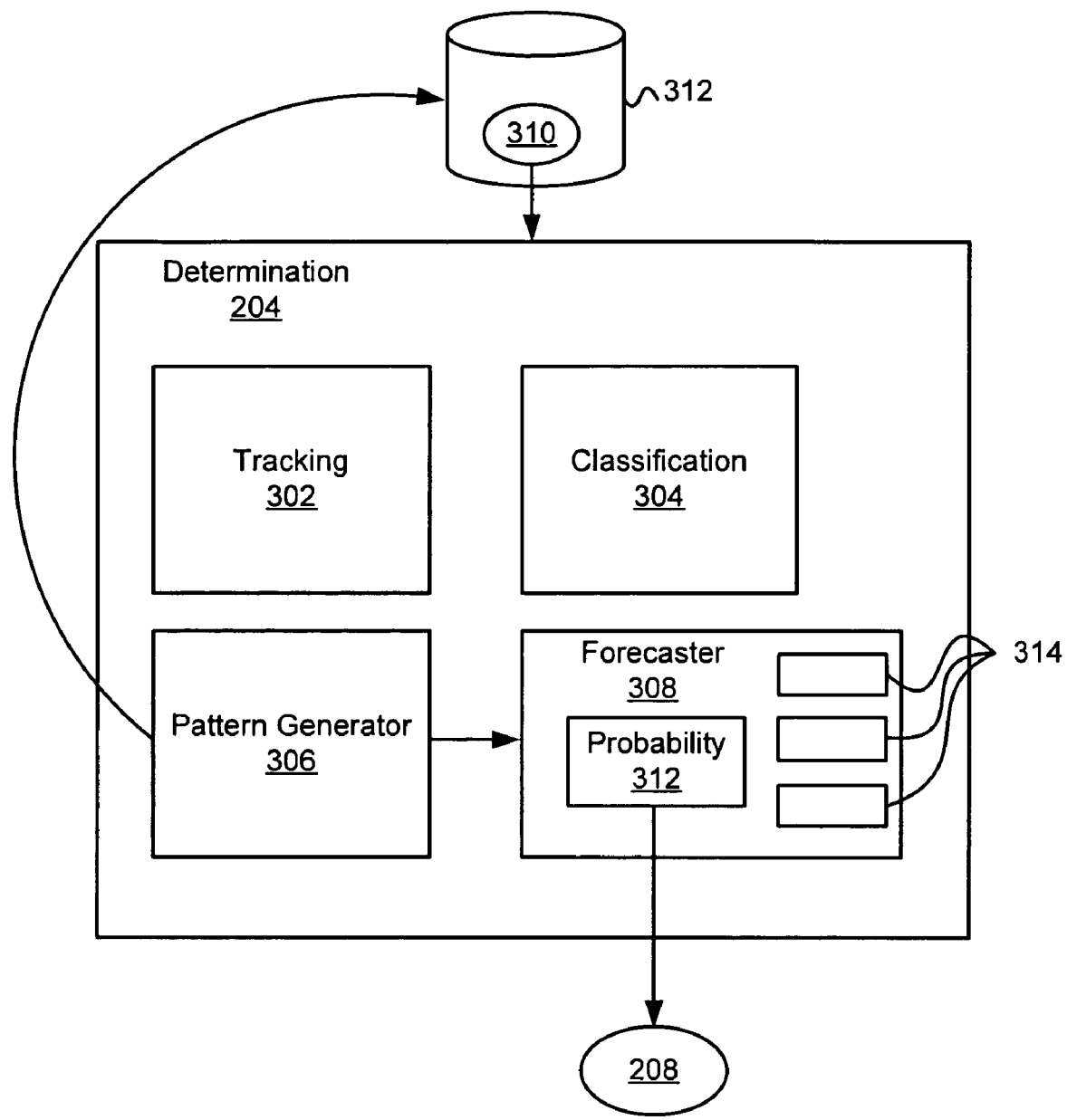
FIG. 3 is a schematic block diagram illustrating a determination module within the apparatus of FIG. 2.

FIG. 3 illustrates details of one embodiment of a determination module 204 configured to determine a motion forecast 208. The determination module 204 may include a tracking module 302, a classification module 304, a pattern generator 306, and a forecaster 308. The tracking module 302 tracks physical movement of the motion-sensitive device 106 in relation to at least one time interval. In one embodiment, the tracking module 302 includes, or is coupled to, a motion detector such as an accelerometer coupled to the motion-sensitive device 106. The tracking module 302 registers a certain number of movements within a time interval. The size of the time interval and sensitivity of movements registered by the tracking module 302 may vary. Preferably, the tracking module 302 monitors movements within a relatively small time interval such as a second or minute. Advantageously, such a time interval allows greater granularity of the movement data collected such that accuracy of predictions based on the movement data can be improved.

In one embodiment, the tracking module 302 is highly sensitive to acceleration. The tracking module 302 may comprise a separate component or may comprise logic that communicates with existing hardware such as an existing accelerometer. Examples of accelerometers that may be used in the tracking module 302 include IMEMS® accelerometers available from Analog Devices of Norwood, Mass.

The classification module 304 communicates with the tracking module 302. The classification module 304 classifies movements detected by the tracking module 302 according to a magnitude of severity. Preferably, the classification module 304 includes one or more severity thresholds of increasing magnitude. As movements are detected by the tracking module 302 that exceed the severity thresholds, the classification module 304 assigns a particular classification to the movement. For example, movements may be classified into categories such as no movement, typical subtle movement or shifting, transport movement, and drop or free-fall movement. Of course a variety of categories may be defined, each associated with a certain magnitude of acceleration within a given time interval.

The pattern generator 306 communicates with the classification module 304 to generate a movement pattern 310. The pattern generator 306 preferably stores the movement pattern 310 on a storage device 312 such as a hard drive. In one embodiment, the pattern generator 306 updates the movement pattern 310 in response to movement variations detected by the tracking module 302 after a movement pattern 310 is defined. A movement variation is defined as a movement that differs from a movement recorded for a corresponding past time period in the movement pattern 310. The pattern generator 306 may update the movement pattern 310 periodically, in response to a user command, or in response to movements detected above a certain severity threshold.

The form and structure of the movement pattern 310 may vary in different embodiments of the present invention. Preferably, the movement pattern 310 correlates classified movements of the motion-sensitive device 106 to a historical passage of time measured in units of hours, days, weeks, months, or the like. For example, the tracking module 302 may detect forty movements of the motion-sensitive device 106 within a five minute time interval. The pattern generator 306 determines that the five minute period was during the 2 o'clock hour in the afternoon. Consequently, the movement pattern 310 may comprise a mapping of movements to times within an hour or day. In addition, the movement pattern may include a mapping of movements within days of a week or weeks of a month.

By mapping movements to a chronologic timeline, the tracking module 302 inherently defines periods when there are substantially no movements. In addition, the movement pattern 310 preferably includes an indication of classification for each movement. The pattern generator 306 may generate a plurality of movement patterns 310 distinguished by time of day, day of week, or the like.

The forecaster 308 preferably defines a motion forecast 208 comprising at least one motionless time interval. The motion forecast 208 is based at least in part on the movement pattern 310. In one embodiment, the motion forecast 208 comprises strictly a prediction of the motionless time intervals. Alternatively or in addition, the motion forecast 208 may comprise a prediction of the classifications and severity of movements that can be expected for the motion-sensitive device 106. In one example, a motion forecast 208 may indicate that there is substantially no motion of the motion-sensitive device 106 between the hours of 10:00 pm and 5:00 am. Consequently, the motion forecast 208 may indicate one motionless time interval between 10:00 pm and 5:00 am. Alternatively, the motion forecast 208 may indicate seven motionless time intervals between 10:00 pm and 5:00 am, one for each hour period.

Preferably, the forecaster 308 combines historical movement information captured in the movement patterns 310, projections based on probabilities from a probability engine 312, one or more prediction algorithms, and one or more motion indicators 314. The probability engine 312 may determine a probability that there will be movement for each time interval included in the motion forecast 208. In particular, the probability engine 312 may determine a probability of movement within the substantially motionless time interval. Typically, this probability is below a probability threshold. The probability threshold maybe user configurable. In one embodiment, substantially motionless time intervals are associated with movement probabilities below about ten percent.

In this manner, different degrees of risk of movement can be communicated in the motion forecast 208. Other logic analyzing the motion forecast 208 can then determine whether the risk of movement is acceptable or not. Preferably, the probability engine 312 uses well known probability algorithms that consider historical information related to time intervals.

The motion indicators 314 may further increase the accuracy of the forecaster 308. Motion indicators 314 are indicators of a potential for motion of the motion-sensitive device 106. The motion indicators 314 may comprise sensors, signals, values, or the like from hardware specific to the present invention or hardware used for other purposes. One example of a motion indicator 314 is a flag indicating whether the motion-sensitive device 106 is coupled to an A/C power source such as a wall socket. If the flag is set, the likelihood that the motion-sensitive device 106 will move is reduced. Another motion indicator 314 may comprise a flag indicating whether a portable electronic device such as a laptop or Personal Digital Assistant (PDA) that houses the motion-sensitive device 106 is coupled to a docking station. Of course those of skill in the art can identify other suitable motion indicators 314 including a motion sensor, a light sensor, a chassis sensor to determine whether a clam-shell type chassis is open or closed, and the like. Each of these motion indicators 314 may provide additional information that the forecaster 308 may use to make the motion forecast 208 more accurate.

Figure 4:
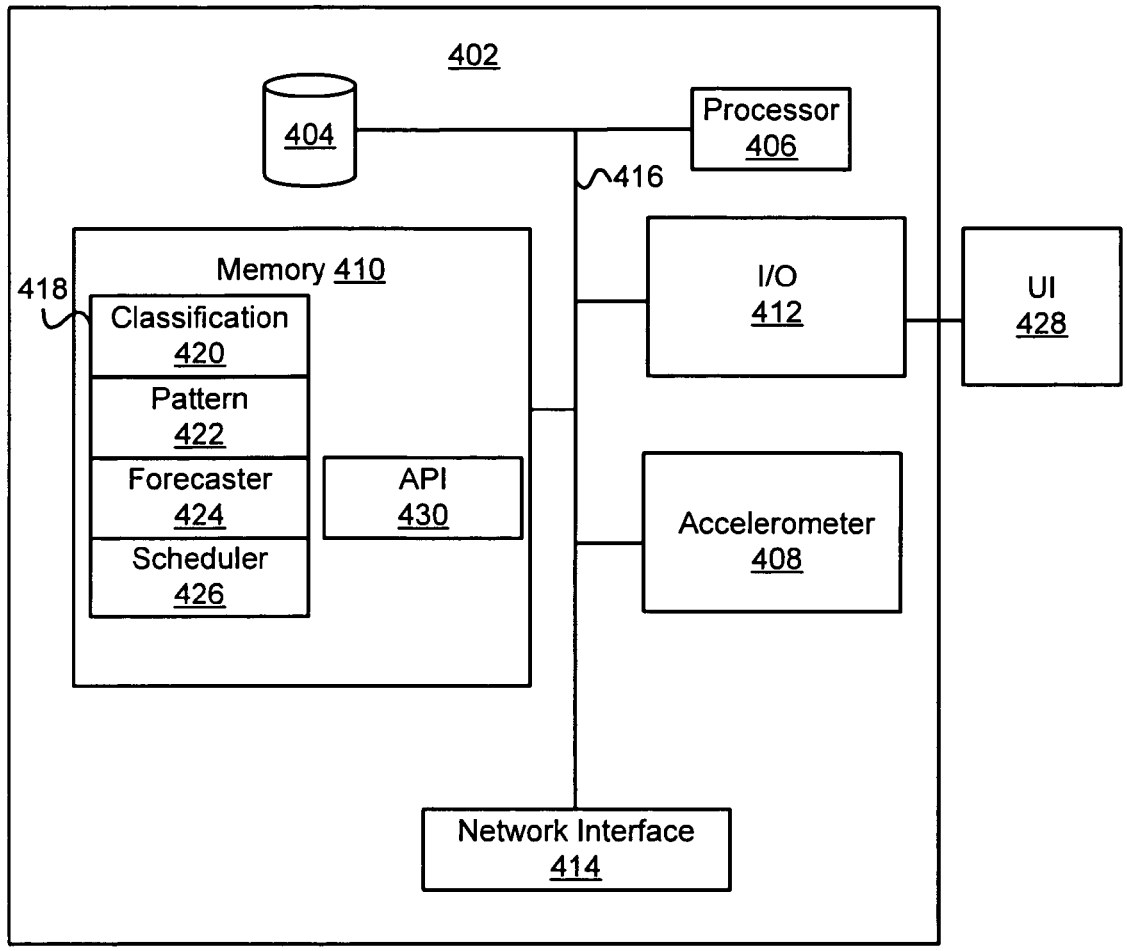
FIG. 4 is a schematic block diagram illustrating an alternative system for protecting a motion-sensitive device.

FIG. 4 illustrates a system 400 for protecting a motion-sensitive device. Preferably, the system 400 is incorporated into a portable electronic device 402 such as a laptop computer, a PDA, a telephone, or the like. The system 400 may include one or more Hard Disk Drives (HDD) 404, a processor 406, an accelerometer 408, and memory 410.

The HDD 404 is well known in the art and may comprise a conventional hard disk drive or a microdrive available from Hitachi Global Storage Technologies of San Jose, Calif. of various capacities. In certain embodiments of the present invention, the HDD 404 serves as the motion-sensitive device 106 (See FIG. 1) discussed above. The HDD 404 typically includes multiple moving parts such as read/write heads connected to arms, spinning platters, and the like that are activated when the HDD 404 is in use. Intensive use of the HDD 404 may cause these internal moving components to move very rapidly. Simultaneous physical movement of the HDD 404 and intensive use can cause damage to the internal components resulting in partial or complete failure of the HDD 404.

The processor 406 is also well known and may execute various instructions to execute tasks defined within operating software such as an operating system and the associated applications running thereon. The processor 406 may communicate with the HDD 404, memory 410, accelerometer 408, and optional I/O module 412 and/or network interface 414 using a system bus 416. The bus 416 may comprise a Peripheral Connect Interface (PCI) bus 416 or the like. The I/O module 412 may include well known I/O drivers and hardware components for communicating output to and receiving input from a user. The network interface 414 is also well known and may include wired or wireless connections to other electronic devices.

The accelerometer 408 may send interrupt signals to the processor 406 in response to detecting movement of the device 402 that exceeds certain threshold levels. Preferably, the accelerometer 408 includes logic to detect and report physical movement of the device 402. One example of an accelerometer 408 suitable for use in the system 400 is an IMEMS® accelerometer available from Analog Devices of Norwood, Mass. The accelerometer 408 may measure acceleration using a capacitive, piezoelectric, piezoresistive, Hall Effect, Magnetoresistive, or heat transfer methodologies. The accelerometer 408 preferably performs substantially the same functions and features as the tracking module 302 described above.

The memory 410 stores logic, data, and executing instructions for the processor 406 to implement one embodiment of a protection module 418. The protection module 418 may include a classification module 420, a pattern generator 422, a forecaster 424, and a scheduler 426. Preferably, the classification module 420 comprises data structures and software logic for implementing the features and functionality of the classification module 304 described in relation to FIG. 3. In addition, the classification module 420 may communicate with the accelerometer 408 to obtain measurements for acceleration events and timing information relating the event to a particular time interval. The classification module 420 may include logic to associate the time interval with a chronologic time period.

The pattern generator 422 and forecaster 424 may similarly include suitable data structures and software logic for implementing the features and functionality of the pattern generator 306 and forecaster 308 described in relation to FIG. 3. The scheduler 426 may comprise data and software suitable for implementing the scheduler 206 described in relation to FIG. 2. In other words, the scheduler 426 preferably schedules use-intensive tasks, that use the HDD 404, for execution within a substantially motionless time interval indicated by the motion forecast from the forecaster 424.

In certain embodiments, the scheduler 426 operates automatically or in response to commands. Automatic operation may comprise the scheduler 426 reviewing tasks provided by an operating system or a system utility. The scheduler 426 may determine the expected duration for a task and then communicate with the forecaster 424 to obtain a forecast 208 (See FIG. 2). The scheduler 426 may then automatically schedule the task for a substantially motionless time interval indicated by the forecast 208.

Alternatively, or in addition, the scheduler 426 may respond to commands. The commands may come from third-party software applications or from a user using a User Interface (UI) 428. In one embodiment, the present invention comprises a published Application Programming Interface (API) 430. The API 430 may provide a plurality of functions and/or data structures that enable the third-party software applications to use the classification module 420, pattern generator 422, forecaster 424, and/or scheduler 426 to gather information about use of a motion-sensitive device 404 and/or physical movement of the motion-sensitive devices 404.

For example, a third-party software application may issue an API call to the present invention using the API 430 to obtain a motion forecast 208. The third-party software application may provide a start time, an operating duration, and a motion-sensitive device indicator. The start time indicates when the third-party software application plans to start a task using the motion-sensitive device. The operating duration indicates how long the third-party software application expects the task to take. In certain embodiments, the pattern generator 422 may derive the operating duration based on historical information for past executions of the task. The motion-sensitive device indicator preferably uniquely identifies the motion-sensitive device that will be involved with the task.

In response to these inputs, the API function may communicate with the forecaster 424 to obtain a motion forecast 208. Preferably, the forecast 208 identifies at least one substantially motionless time interval that is preferably of greater length than the operating duration. Alternatively, the substantially motionless time interval may last for a majority of the operating duration.

In certain embodiments, the third-party software application comprises utilities provided in an operating system. The utilities may be used for maintenance, quality control, security, and the like. Examples of such utilities include hard drive defragmentation tools, spyware scanning tools, anti-virus scanning tools, and the like. These utilities may interface with the present invention through the API 430 automatically.

Alternatively, each third-party software application may involve a user through a separate User Interface UI 428. Alternatively, certain embodiments provide a UI 428 that may be used for scheduling a plurality of tasks. For example, in certain operating systems, such as MICROSOFT WINDOWS® operating system, certain tasks may be scheduled by a user. The UI 428 may comprise a set of wizard assistance windows or a single window allowing a user to edit the properties and/or scheduling of the task.

In one embodiment, the UI 428 may include a button or menu item allowing the forecaster 424 to propose a start time for the task. The start time may correspond to the substantially motionless time interval such that the task starts and completes within the substantially motionless time interval. Based on the user-defined start time and the expected task duration, the UI 428 may prompt the user to manually schedule the task based on the motion forecast 208. The prompting may be done in response to active manual scheduling by the user. Alternatively, the system 400 may passively observe user actions and thereby conclude that the user is scheduling a task that could benefit from the information in the motion forecast 208.

In certain embodiments, configuration settings may determine how closely manual scheduling corresponds to motionless time intervals in the forecast 208. For example, in one embodiment, the start time may precede the motionless time interval by a certain percentage of the expected task duration. Alternatively, configuration settings may dictate that the task be scheduled to at least start within the motionless time.

In yet another embodiment, the user is permitted to schedule the task for anytime and the UI 428 is configured to advise the user of a start time that corresponds with the motion forecast and a motionless time interval. This advice may be provided in a pop-up window and the user may be permitted to accept or reject the suggestion. In this manner, manual scheduling may be permitted while other suggested scheduling times are advised.

Figure 5:
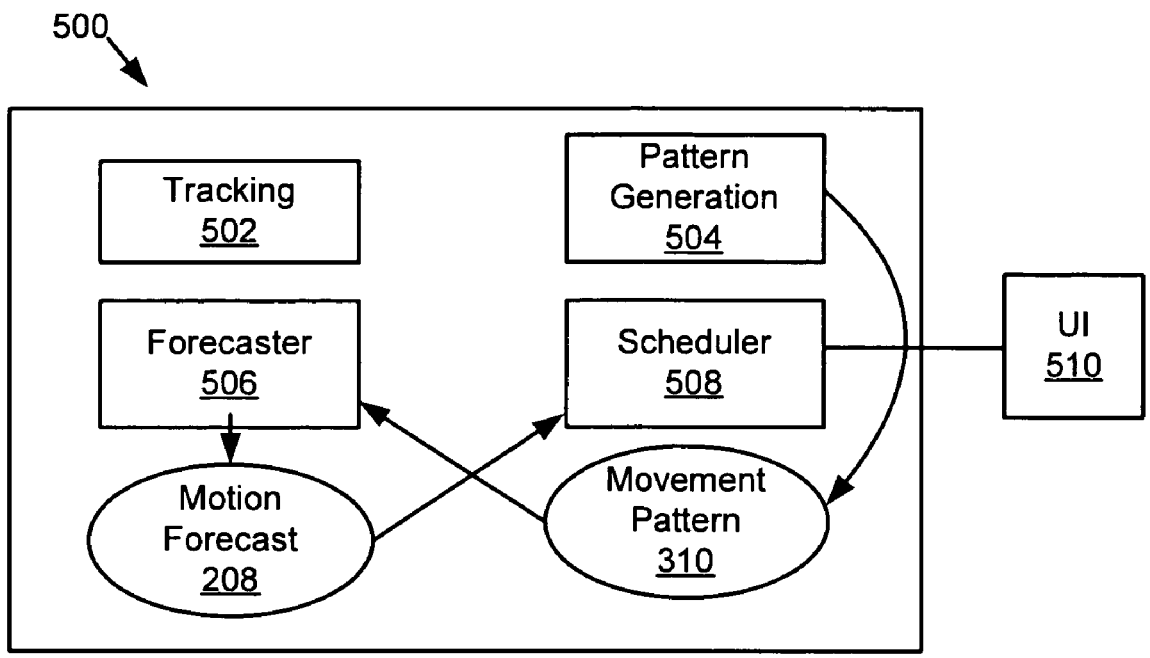
FIG. 5 is a schematic block diagram illustrating an alternative apparatus for protecting a motion-sensitive device.

FIG. 5 illustrates one embodiment of an apparatus 500 for protecting a motion-sensitive device such as storage device 106. The apparatus 500 includes a tracking module 502, a pattern generator 504, a forecaster 506, a scheduler 508, and a UI 510. The tracking module 502 is configured to track physical movement of a motion-sensitive device 106. The tracking module 502 may track physical movement in relation to at least one reference time interval. The reference time interval is a time period such as a millisecond, second, minute, hour, day, week, month, or the like. Preferably, the reference time interval is also correlated to a chronological period of time such as a time period within a particular day, month, and/or year.

The tracking module 502 may include an accelerometer similar to that described above. Movements above a certain threshold may cause the tracking module 502 to record a movement event. Preferably, the movement events are stored along with an identifier and a timestamp that correlates to a chronological period of time. Alternatively, the tracking module 502 may be coupled to the motion-sensitive device 106 instead of the apparatus 500.

The pattern generator 504 and forecaster 506 may operate in substantially the same manner as the tracking module 302 and forecaster 308 described above in relation to FIG. 3. The scheduler 508 and UI 510 may operate in substantially the same manner as the scheduler 426 and UI 428 described above in relation to FIG. 4. The forecaster produces a motion forecast 208 in response to a command from the scheduler 508. The pattern generator 504 may generate one or more movement pattern 310 periodically or based on the number of movements detected.

In contrast to the determination module 204 of FIG. 3 and the system 400 of FIG. 4, the apparatus 500 may not include a classification module 420. Consequently, the movement pattern 310 may not include a classification indicator. Instead, each movement, above a sensitivity level, may be tracked by the tracking module 502, incorporated into the movement pattern 310 by the pattern generator 504, and included in the motion forecast 208 by the forecaster 506.

Consequently, a user using the UI 510 or a software application interacting with the apparatus 500 through an API 430 (See FIG. 4) may classify the information in the motion forecast 208. For example, the motion forecast 208 may include a severity indicator that is made available through the UI 510 or API 430. One example motion forecast 208 may predict that movement of the motion-sensitive device 106 is anticipated for the coming weekend as the motion-sensitive device 106 has historically been transported from one workspace to another. Advantageously, the example motion forecast 208 may also indicate the severity level of the movement. A user may configure the scheduler 508 to trigger a use-intensive task based on projected periods when the severity level is below a certain level. In this manner, the classification of the movements in the motion forecast 208 is left to the user. Consequently, the classification may be more flexible than the classifications a classification module 420 might provide.

Figure 6:
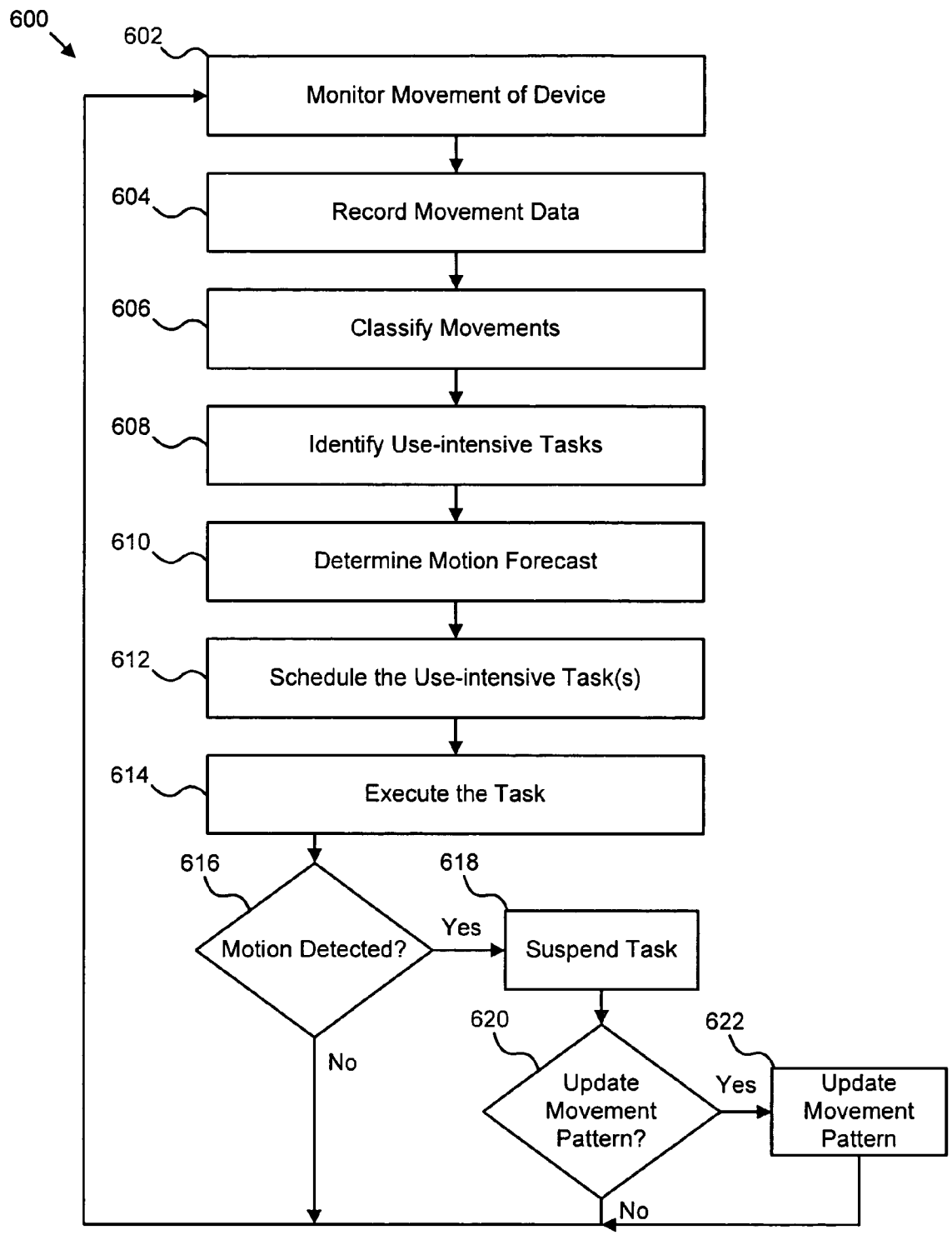
FIG. 6 is a schematic flow chart diagram illustrating one embodiment of a method for protecting a motion-sensitive device.

FIG. 6 illustrates one embodiment of a method 600 for protecting a motion-sensitive device. The method 600 typically includes the steps necessary to implement the functionality provided and described above in relation to the systems 100, 400 and apparatus 500 of the present invention.

In one embodiment, the method 600 begins by monitoring 602 physical movement of the motion-sensitive device 106. Monitoring may be performed by the tracking module 302, 502, an accelerometer 408, or the like. Next, the pattern generator 422 records 604 the movement data associated with the motion-sensitive device 106 in the form of a movement pattern 310. Of course the pattern generator 306, 422 and tracking module 302 may track and monitor a plurality of motion-sensitive devices 106. In certain embodiments, a classification module 304, 420 classifies 606 the movements based on a severity indicator. The classification may occur on movement data before movement patterns 310 are generated. Alternatively, the movement patterns 310 may include severity indicators such that the movement classification module 304, 420 classifies 606 the movement patterns 310.

Next, the identification module 202 identifies 608 use-intensive tasks involving the motion-sensitive device 106. In certain embodiments, the use-intensive tasks are identified as those performing a predefined number of operations within a time interval. Consequently, the identification module 202 may monitor use of the motion-sensitive device 106 by any task, a class of tasks, or predefined tasks. The predefined number of operations and time interval may be user configurable such that the user can control which operations/tasks are considered use-intensive. A user may change the predefined number of operations and a time interval by editing a configuration file or using a user interface 428.

Automatically, or in response to a request from a third-party software application or a user, the determination module 204 and/or forecaster 308, 424 determines 610 a motion forecast 208. Preferably, the motion forecast 208 covers time intervals with sufficient granularity such as minutes or seconds. In this manner, the likelihood that suitable motionless time intervals exist is higher.

Preferably, the scheduler 206, 426, 508 schedules 612 an identified use-intensive task to operate during one or more substantially motionless time intervals. The identified use-intensive tasks are preferably not time sensitive meaning these tasks can be performed at any time within a particular time window. The window may be a twenty-four hour period, a five or seven day period, or the like. The scheduler 206, 426, 508 may operate automatically, in response to an API call, or in response to a user command.

According to the schedule, the execution module 214 executes 614 the identified use-intensive tasks. In one embodiment, the scheduler 206, 426, 508 executes 614 the identified use-intensive tasks. Preferably, the use-intensive tasks complete before a motionless time interval ends.

During task execution, the detector 216 or tracking module 302, 502, 408 may continue to monitor movement of the motion-sensitive device 106. In certain circumstances, a substantially motionless time interval is interrupted by movement of the motion-sensitive device 106. To account for this possibility, protection module 114 determines 614 whether the motion-sensitive device 106 moves above a certain threshold during execution of identified use-intensive tasks. If so, the suspension module 218 suspends 618 the use-intensive tasks. In certain embodiments, the suspension module 218 may additionally trigger other steps to protect the motion-sensitive device 106 such as parking the heads of a hard drive. If no movement is detected, the tasks may complete or continue execution and the method 600 may continue monitoring movement of the motion-sensitive device 106.

In one embodiment, if a task is suspended due to movement of the motion-sensitive device 106, a task manager 212 may determine 620 whether to update the movement pattern 310. The task manager 212 may execute an algorithm to determine whether the movement is representative of a pattern that justifies changing the movement pattern 310 or an anomaly that can be ignored. If the task manager 212 decides to update the movement pattern 310, the determination module 204 may update 622 the movement pattern 310 to reflect the movement that was detected. Once an update is made or if the task manager 212 determines that an update is not necessary, the method 600 returns to monitoring in step 602.

The method 600 may initiate automatically in the form of a windows service or daemon and terminate when a computer system is shutdown. Alternatively, a user may initiate and shutdown the method 600. Preferably, the method 600 continuously performs steps 602-604 such that movement patterns 310 and motion forecasts 208 can be constantly improved and refined.

The present invention minimizes operation of motion-sensitive devices such as hard drives during periods of high risk of damage such during movement of the motion-sensitive device. In particular, the present invention facilitates scheduling of use-intensive tasks during substantially motionless time intervals to minimize the coincidence of physical movement of the motion-sensitive device and operation of use-intensive tasks. Furthermore, the present invention may interrupt use-intensive tasks operating when the motion-sensitive device is moved.

Many functional units described herein are labeled as components, in order to more particularly emphasize their implementation independence. For example, a component may be implemented as a hardware circuit comprising custom VLSI circuits or gate arrays, off-the-shelf semiconductors such as logic chips, transistors, or other discrete components. A component may also be implemented in programmable hardware devices such as field programmable gate arrays, programmable array logic, programmable logic devices or the like.

Components may be implemented in software for execution by various types of processors. An identified component of executable code may, for instance, comprise one or more physical or logical blocks of computer instructions which may, for instance, be organized as an object, procedure, or function. Nevertheless, the executables of an identified component need not be physically located together, but may comprise disparate instructions stored in different locations which, when joined logically together, comprise the component and achieve the stated purpose for the component.

Indeed, a component of executable code may be a single instruction, or many instructions, and may even be distributed over several different code segments, among different programs, and across several memory devices. Similarly, operational data may be identified and illustrated herein within components, and may be embodied in any suitable form and organized within any suitable type of data structure. The operational data may be collected as a single data set, or may be distributed over different locations including over different storage devices.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of programming, software components, user selections, network transactions, database queries, database structures, hardware components, hardware circuits, hardware chips, etc., to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus for protecting a hard disk drive (HDD), the apparatus comprising:
    a semiconductor device storing executable code;
    a processor executing the executable code, the executable code comprising
        an identification module identifying a use-intensive task involving the HDD wherein the use-intensive task has a use frequency that exceeds a use frequency threshold;
        a tracking module tracking movements of the HDD in relation to at least one reference time interval;
        a classification module classifying the movements based on a severity threshold;
        a determination module determining a motion forecast that predicts a motionless time interval of at least one hour within a 24 hour period and comprising a pattern generator configured to generate a movement pattern representative of movement of the HDD during the 24 hour period; and
        a scheduler scheduling the use-intensive task such that the use-intensive task executes within the motionless time interval.

2. The apparatus of claim 1, the executable code further comprising,
    a monitor monitoring use of the HDD by at least one operating task; and
    a task manager recording use data representative of use of the HDD by the at least one operating task.

3. The apparatus of claim 1, the executable code further comprising,
    an execution module executing the use-intensive task within the motionless time interval;
    a detector detecting motion of the HDD during the motionless time interval; and
    a suspension module suspending operation of the use-intensive task in response to the detected motion exceeding a suspension threshold.

4. The apparatus of claim 1, wherein the pattern generator updates the movement pattern in response to movement variations occurring after the movement pattern is generated.

5. The apparatus of claim 1, wherein the determination module comprises a probability engine defining a probability of movement of the HDD within the motionless time interval, the probability being below a probability threshold.

6. The apparatus of claim 5, wherein the determination module further comprises one or more motion indicators indicative of motion potential for the hard disk drive, the probability engine modifying the probability of movement based on the motion indicators.

7. A system for protecting a HDD, the system comprising:
the HDD;
a processor executing executable code;
an accelerometer coupled to the processor and the HDD, the accelerometer measuring acceleration events of the HDD within a predefined time interval;
a memory storing the executable code, the executable code comprising,
 an identification module identifying a use-intensive task involving the HDD wherein the use-intensive task has a use frequency that exceeds a use frequency threshold;
 a tracking module tracking acceleration events of the HDD in relation to at least one reference time interval;
 a classification module classifying the acceleration events based on a severity threshold;
 a pattern generator generating a movement pattern representative of movement of the HDD during the predefined time interval;
 a forecaster defining a motion forecast comprising at least one motionless time interval of at least one hour within a 24 hour period, the motion forecast based at least in part on the movement pattern; and
 a scheduler scheduling the use-intensive task such that the use-intensive task executes within the motionless time interval.

8. The system of claim 7, the executable code further comprising,
a monitor monitoring use of the HDD by at least one operating task; and
a task manager recording use data representative of use of the HDD by the at least one operating task.

9. The system of claim 8, wherein the pattern generator updates the movement pattern in response to movement variations occurring after the movement pattern is generated.

10. The system of claim 9, wherein the forecaster comprises a probability engine defining a probability of movement of the HDD within the motionless time interval, the probability being below a probability threshold.

11. The system of claim 10, wherein the forecaster further comprises one or more motion indicators indicative of motion potential for the HDD, the probability engine modifying the probability of movement based on the motion indicators.

12. The system of claim 10, the forecaster further defining a motion forecast for a third-party software application in response to a start time and an operating duration provided by the third-party software application.

13. A method for protecting a HDD, the method comprising:
identifying, by use of a processor, a task involving the HDD wherein the use-intensive task has a use frequency that exceeds a use frequency threshold;
tracking movements of the HDD in relation to at least one reference time interval;
classifying the movements based on a severity threshold;
generating a movement pattern representative of movement of the HDD during a 24 hour period;
determining a motion forecast that predicts a motionless time interval of at least one hour within the 24 hour period; and
scheduling the use-intensive task such that the use-intensive task executes within the motionless time interval.

14. The method of claim 13, further comprising updating the movement pattern in response to movement variations occurring after the movement pattern is generated.

15. The method of claim 13, further comprising,
monitoring use of the HDD by at least one operating task;
recording use data representative of use of the HDD by the at least one operating task; and
classifying one or more operating tasks as use-intensive tasks based on the use frequency threshold.

16. The method of claim 13, wherein scheduling further comprises prompting a user to manually schedule the use-intensive task according to the motion forecast during the motionless time interval within the 24 hour period.

17. The method of claim 13, further comprising,
executing the use-intensive task within the motionless time interval;
detecting motion of the HDD during the motionless time interval; and
suspending the use-intensive task in response to the detected motion exceeding a suspension threshold.

18. An apparatus for protecting a HDD, the apparatus comprising:
a semiconductor device storing executable code;
a processor executing the executable code, the executable code comprising
 an identification module identifying a use-intensive task involving the HDD wherein the use-intensive task has a use frequency that exceeds a use frequency threshold;
 a tracking module tracking movements of the HDD in relation to at least one reference time interval;
 a classification module classifying the movements based on a severity threshold;
 a pattern generator generating a movement pattern representative of movement of the HDD during a 24 hour period;
 a forecaster defining a motion forecast that predicts at least one motionless time interval of at least one hour within the 24 hour period, the motion forecast based at least in part on the movement pattern; and
 a scheduler scheduling a use-intensive task in response to the motion forecast comprising the at least one motionless time interval, the use-intensive task scheduled to execute within the at least one motionless time interval.

19. The apparatus of claim 18, wherein the motion forecast defines a probability of movement of the HDD within the at least one motionless time interval, the probability being below a probability threshold.

20. The apparatus of claim 18, the forecaster further defining a motion forecast for a third-party software application in response to a start time and an operating duration provided by the third-party software application.

21. A semiconductor device storing executable code executed by a processor to perform operations comprising:
an operation to identify a use-intensive task involving the HDD wherein the use-intensive task has a use frequency that exceeds a use frequency threshold;
an operation to track movements of the HDD in relation to at least one reference time interval;
an operation to classify the movements based on a severity threshold;
an operation to generate a movement pattern representative of movement of the HDD during a 24 hour period;

an operation to determine a motion forecast that predicts a motionless time interval of at least one hour within the 24 hour period; and an operation to schedule the use-intensive task such that the use-intensive task executes within the motionless time interval.

22. The semiconductor device of claim 21, further comprising an operation to send a motion forecast a third-party software application in response to a start time and an operating duration provided by the third-party software application.

* * * * *

UNITED STATES PATENT AND TRADEMARK OFFICE
CERTIFICATE OF CORRECTION

PATENT NO. : 7,600,054 B2 Page 1 of 1
APPLICATION NO. : 11/273240
DATED : October 6, 2009
INVENTOR(S) : Cromer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 745 days.

Signed and Sealed this

Fifth Day of October, 2010

David J. Kappos
*Director of the United States Patent and Trademark Office*